US008871218B2

(12) United States Patent
Zwijsen et al.

(10) Patent No.: US 8,871,218 B2
(45) Date of Patent: *Oct. 28, 2014

(54) INFANT NUTRITIONAL COMPOSITIONS FOR PREVENTING OBESITY

(75) Inventors: Renate Maria Louise Zwijsen, Utrecht (NL); Gelske Speelmans, Wageningen (NL); Eline Marleen van der Beek, Wageningen (NL); Gunther Boehm, Echzell (DE)

(73) Assignee: N.V. Nutricia, Zoetermeer (NL)

( * ) Notice: Subject to any disclaimer, the term of this patent is extended or adjusted under 35 U.S.C. 154(b) by 145 days.

This patent is subject to a terminal disclaimer.

(21) Appl. No.: 13/357,109

(22) Filed: Jan. 24, 2012

(65) Prior Publication Data

US 2012/0121757 A1  May 17, 2012

Related U.S. Application Data

(62) Division of application No. 12/158,876, filed as application No. PCT/NL2006/050329 on Dec. 22, 2006, now Pat. No. 8,119,142.

(30) Foreign Application Priority Data

Dec. 23, 2005  (EP) ..................................... 05077972
Nov. 2, 2006  (NL) ................. PCT/NL2006/050274

(51) Int. Cl.
*A61K 36/02* (2006.01)
*A61K 31/70* (2006.01)
*A61K 31/20* (2006.01)
*A23L 1/29* (2006.01)
*A61K 31/198* (2006.01)
*A23L 1/30* (2006.01)
*A61K 35/20* (2006.01)
*A61K 31/185* (2006.01)

(52) U.S. Cl.
CPC .............. *A23L 1/3008* (2013.01); *A23L 1/296* (2013.01); *A61K 31/198* (2013.01); *A23V 2002/00* (2013.01); *A61K 31/20* (2013.01); *A61K 35/20* (2013.01); *A61K 31/185* (2013.01)
USPC .......................... 424/195.17; 514/23; 514/558

(58) Field of Classification Search
USPC ................. 424/195.17; 514/23, 558
IPC .................. A61K 36/02,31/70, 31/20
See application file for complete search history.

(56) References Cited

U.S. PATENT DOCUMENTS

| 6,149,964 | A * | 11/2000 | Theuer et al. ................. 426/614 |
| 6,194,009 | B1 * | 2/2001 | Kamarel .......................... 426/72 |
| 6,413,557 | B1 * | 7/2002 | Lee ................................. 424/757 |
| 6,579,551 | B1 * | 6/2003 | Theuer et al. ................. 426/321 |
| 6,613,367 | B1 * | 9/2003 | Wells et al. ...................... 426/72 |
| 6,753,350 | B1 * | 6/2004 | Hansen et al. ................. 514/560 |
| 6,998,392 | B2 * | 2/2006 | Clandinin et al. .............. 514/54 |
| 2003/0104078 | A1 * | 6/2003 | Barrett-Reis et al. ......... 424/727 |
| 2004/0013787 | A1 * | 1/2004 | Theuer .......................... 426/601 |
| 2004/0071824 | A1 * | 4/2004 | Van Laere et al. .............. 426/71 |
| 2004/0265462 | A1 * | 12/2004 | Carlson ......................... 426/580 |
| 2008/0125346 | A1 * | 5/2008 | Beermann et al. ................ 514/2 |
| 2011/0250317 | A1 * | 10/2011 | Secretin ......................... 426/61 |

FOREIGN PATENT DOCUMENTS

| EP | 0 484 266 | 5/1992 |
| WO | WO 03/005836 | 1/2003 |
| WO | WO 2006/009437 | 1/2006 |
| WO | WO 2006/057551 | 6/2006 |
| WO | WO 2006/069918 | 7/2006 |
| WO | WO 2006/091103 | 8/2006 |

OTHER PUBLICATIONS

McVeagh, P. Pacific Health Dialog, 1994. vol. 1, No. 2, p. 43-51.*
Prentice, A. Food and Nutrition Bulletin. 1996. vol. 17, No. 4, 11 pages.*
Website publication from WebMD.com entitled "Obesity-Overview". Downloaded Dec. 28, 2010. 2 pages. Obtainable online from website http://www.webmd.com/diet/tc/obesity-overview.*
Website publication from WebMD.com entitled "Obesity-Cause". Downloaded Dec. 28, 2010. 2 pages. Obtainable online from website http://www.webmd.com/diet/tc/obesity-cause.*
Ailhaud, G. et al.: "Temporal changes in dietary fats: role of n-6 polyunsaturated fatty acids in excessive adipose tissue development and relationship to obesity." *Progress in Lipid Research*, 45(3):203-236 (2006).
Czeczelewski, Jan et al.: "Nutritional status versus diet composition of 10-15—year-old children from the Central-East Poland." *Polish Journal of Food and Nutrition Sciences*, 15(2):221-226 (2006).

* cited by examiner

*Primary Examiner* — Chris R Tate
(74) *Attorney, Agent, or Firm* — Browdy and Neimark, PLLC

(57) ABSTRACT

The present invention relates to a method for preventing obesity later in life by administering a certain nutritional composition to an infant between 0 and 36 months of age.

18 Claims, No Drawings

INFANT NUTRITIONAL COMPOSITIONS FOR PREVENTING OBESITY

This application is a divisional of U.S. Ser. No. 12/158,876 (allowed), the U.S. national phase entry date of which was Jun. 23, 2008.

FIELD OF THE INVENTION

The present invention relates to preventing obesity later in life by administering a particular nutritional composition to non-obese infants with the age below 3 years.

BACKGROUND OF THE INVENTION

Breast-feeding is the preferred method of feeding infants. However, there are circumstances that make breast-feeding impossible or less desirable. In those cases infant formulae are a good alternative. The composition of modern infant formulae is adapted in such a way that it meets many of the special nutritional requirements of the fast growing and developing infant.

Still it seems that improvements can be made towards the constitution of infant milk formulae. For example little is known about the effects of ingredients in the infant formulae on obesity later in life. The present invention relates to such future health.

WO 2005063050 describes a method of increasing lean body mass and reducing fat body mass in infants by administering to an infant, term or preterm, a nutritional formula comprising a source of DHA and ARA. WO 2006057551 relates to an infant nutrition comprising at least one protease inhibitor, a process for preparing such an infant nutrition and use of the infant nutrition for the treatment and/or prevention of childhood obesity and secondary disorders resulting from childhood obesity. WO 03005836 describes dietary products for infant, child and adult nutrition which possess adequate levels and ratios of medium chain fatty acids and omega-polyunsaturated fatty acids. Consumption of these dietary products can contribute to the prevention of obesity in developing individuals and can contribute to a reduction in body fat mass in individuals who are trying to loose weight or reduce body fat mass (e.g., obese individuals). WO 2006069918 describes a method of continuously reducing the circulating level of insulin like growth factor 1 (IGF-1) in the first few months of the life of an infant by administering to the infant a nutritional composition comprising proteins in an amount such that the composition contains less than 2.25 g of protein per 100 kcal. As IGF-1 is known to be a key control point in nutritional regulation of growth, this may offer a method of reducing the risk of developing obesity later life. Aillaud et al., 2006, *Progress in Lipid research* 45:203-206, discusses the role of n-6 polyunsaturated fatty acids in the excessive adipose tissue development and relationship to obesity.

SUMMARY OF THE INVENTION

During infancy, body fat, especially subcutaneous fat, has the important function to maintain an adequate body temperature and to store energy. Therefore, it is not desirable to generally reduce body fat mass in infants, because this may interfere with good growth and development. Hence, a main aim of the present invention is to design a nutrition to be administered to an infant, which ensures maintenance of normal body composition, growth and development during infancy but which reduces the accumulation of excess body fat mass later in life (i.e. after infancy), preferably during adolescence and/or adulthood.

The inventors experimentally evidenced that early-in-life administering nutrition wherein the lipid component is relatively low in linoleic acid (LA) and wherein the linoleic acid/alpha-linolenic acid (LA/ALA) ratio is low, results in a decreased fat mass accumulation, particularly a decreased visceral fat mass accumulation, later in life. In these experiments, mice received specific nutrition (low in LA and low LA/ALA) early-in-life, while a control group did not receive the specific nutrition. At the later-in-life stage the animal groups received the same diet high in saturated fat. Surprisingly, no effect on growth and total body fat mass was observed during the infancy stage, but, compared to the control group, a decreased total body fat mass, and specifically a decreased visceral fat mass, was observed in mice at the adolescence and adulthood stage of life which had been fed this experimental nutrition during infancy. The outcome of the experiments is indicative for the effect of the present infant nutrition composition in the development of obesity later in life, particularly at an age above 36 months, i.e. during childhood (age 3-12 years), adolescence (age 13-18 years) and adulthood (age above 18 years).

The present invention thus relates to a method for preventing the development of obesity of a human infant with an age above 36 months, in other words for preventing development of obesity later-in-life, said method comprising the administration to an infant below 36 months of age a nutritional composition comprising a lipid, protein and digestible carbohydrate component wherein the lipid component comprises linoleic acid (LA) and alpha-linolenic acid (ALA) in a weight ratio of LA/ALA between 2 and 7; less than 15 wt. % LA based on total fatty acids; and at least 1 wt. % ALA based on total fatty acids.

For certain jurisdictions the invention is also described as the use of a composition comprising a lipid, protein and digestible carbohydrate component wherein the lipid component comprises (i) linoleic acid (LA) and alpha-linolenic acid (ALA) in a weight ratio of LA/ALA between 2 and 7; (ii) less than 15 wt. % LA based on total fatty acids; and (iii) at least 1 wt. % ALA based on total fatty acids, for the manufacture of a nutritional composition to be administered to a (non-obese) infant with the age below 36 months for the prevention of obesity. The inventions is preferably described as a composition to be administered to a non-obese human with the age below 36 months, said composition comprising a lipid, protein and digestible carbohydrate components, wherein the lipid component comprises linoleic acid (LA) and alpha-linolenic acid (ALA) in a weight ratio of LA/ALA between 2 and 7; less than 15 wt. % LA based on total fatty acids; and over 1 wt. % ALA based on total fatty acids for preventing the development of a disorder, particularly obesity, when said human has an age above 36 months.

In addition the inventors recognized that designing an infant nutrition which is low in LA and with a low ratio of LA/ALA in order to prevent obesity later-in-life may impair the bioavailability and incorporation of LA and the n-6 long chain polyunsaturated fatty acids (LC-PUFA) which are biosynthesized from LA, such as arachidonic acid (AA), in membranes of neurological tissues such as brain and retina. LA and particularly AA are an important precursor for brain phospholipids, and therefore of utmost importance in infants, particularly for development of the visual system, the brain, intelligence and cognitive skills (later-in-life). In order to prevent side effects of the low LA it is important to stimulate the membrane formation and including components which support membrane development in the brain and other neurological tissues. Hence, the present invention provides a low LA nutrition which reduces the accumulation of excess body fat mass later in life (i.e. after infancy), and comprising at least one selected from (i) phospholipids; (ii) sphingolipids; (iii) cholesterol; and/or (iv) uridine and choline. The inclusion of this component in the present low LA formula enhances bioavailability of PUFA, particularly n-6 PUFA, for incorporation in membranes and/or decreases n-6 (LC-) PUFA oxidation. The mixture of uridine and choline increases the formation of phospholipids. Hence, including one or more of these components advantageously stimulates an optimal brain development as it increases the quantities of membrane phospholipids per cell, when included in the present low LA composition. It is a further aim of the present invention to provide a low LA formula which gives a low insulin response.

DETAILED DESCRIPTION OF THE INVENTION

The present invention provides the use of a composition comprising a lipid, protein and digestible carbohydrate component wherein the lipid component comprises:
 (i) linoleic acid (LA) and alpha-linolenic acid (ALA) in a weight ratio of LA/ALA between 2 and 7;
 (ii) less than 15 wt. % LA based on total fatty acids; and
 (iii) at least 1 wt. % ALA based on total fatty acids,
 and wherein the composition further comprises at least one selected from the group consisting of
 (a) 0.5 to 20 wt. % phospholipids based on total fat;
 (b) 0.5 to 20 wt. % sphingolipids based on total fat;
 (c) 0.005 to 10 wt. % cholesterol based on total fat; and
 (d) 0.035 to 1 wt. % choline based on dry weight of the composition and 0.001 to 0.1 wt. % uridine based on dry weight of the present composition,
 for the manufacture of a nutritional composition to be administered to a (non-obese) infant with the age below 36 months for the prevention of obesity.

In a further aspect the present invention provides the use of a composition comprising a lipid, protein, digestible carbohydrate (e.g. the present low LA composition) and cholesterol for the manufacture of a nutritional composition to be administered to an infant with the age below 36 months for the prevention of cardiovascular disease, atherosclerosis, and/or blood cholesterol levels later in life.

Obesity

The present composition is administered to a non-obese human infant with the age below 36 months, preferably below 18 months, more preferably below 12 months, even more preferably below 6 months. Preferably the present composition is administered to a non-overweight human with the age below 36 months, preferably below 18 months, more preferably below 12 months, even more preferably below 6 months of age. The absence or presence of obesity and/or overweight in an infant can suitably be determined by a physician. Typically, a non-obese infant below 36 months of age has gender specific weight-for-length below the 95$^{th}$ percentile, more preferably below the 85$^{th}$ percentile. Gender specific weight-for-length percentiles have been published by Center for Disease Control and Prevention (CDC) in 2000. Likewise the presence or absence of obesity and/or overweight in a human subject above 36 months of age can be easily determined by a physician and/or with the gender specific weight-for-length percentiles published by CDC.

Health related problems are especially associated with a special form of obesity, namely central obesity. Preferably the composition is used to prevent central obesity later-in-life. The term 'central obesity' refers to a condition with increased visceral fat mass. A waist circumference above 102 cm in adult man or above 88 cm in adult women indicates central obesity. For children of 3-19 years old appropriate cutoffs for age- and sex-dependent waist circumferences can be found in Taylor et al., 2000, *Am J Clin Nutr* 72:490-495.

Low LA Composition

Herein LA refers to linoleic acid (18:2 n6); ALA refers to α-linolenic acid (18:3 n3); LC-PUFA refers to long chain polyunsaturated fatty acids and/or acyl chains comprising at least 20 carbon atoms in the fatty acyl chain and with 2 or more unsaturated bonds; DHA refers to docosahexaenoic acid (22:6, n3); EPA refers to eicosapentaenoic acid (20:5 n3); ARA refers to arachidonic acid (20:4 n6); DPA refers to docosapentaenoic acid (22:5 n3), and DHGLA refers to dihomogammalinolenic acid (20:3 n6). Medium chain fatty acids (MCFA) refer to fatty acids and/or acyl chains with a chain length of 6, 8 or 10 carbon atoms. MCFA may also be referred to as medium chain triglycerides (MCT).

The present inventors have found that specific compositions that have a low LA/ALA ratio and that are low in LA prevent the occurrence of obesity, especially central obesity. Particularly the administration of a nutritional composition comprising (i) a LA/ALA weight ratio between 2 and 7 and (ii) a low LA content (<15 wt. % based on total fatty acids), resulted in a decreased obesity later in life.

The present composition comprises lipid. LA should be present in a sufficient amount in order to promote a healthy growth and development, yet in an amount as low as possible to prevent occurrence of obesity later in life. The composition therefore comprises less than 15 wt. % LA based on total fatty acids, preferably between 5 and 14.5 wt. %, more preferably between 6 and 12 wt. %. Based on total dry weight of the composition the present composition preferably comprises 1.5 to 5 wt. % LA. When in liquid form, e.g. as ready-to-drink formula, the LA content is preferably between 0.2 and 0.55 g LA per 100 ml of the liquid composition. The LA preferably provides between 4 to 8% of total calories in the present composition.

ALA should be present in a sufficient amount to promote a healthy growth and development of the infant. The present composition therefore comprises at least 1.0 wt. % based on total fatty acids. Preferably the composition comprises at least 1.6 wt. % ALA based on total fatty acids, more preferably at least 2.0 wt. %. Preferably the composition comprises less than 10 wt. % ALA, more preferably less than 5.0 wt. % based on total fatty acids. Based on total dry weight of the composition the present composition preferably comprises at least 0.10 wt. % ALA, preferably between 0.10 and 0.8 wt. % ALA. When in liquid form, e.g. as ready-to-drink formula, the ALA content is preferably at least 30 mg ALA per 100 ml of the liquid composition, preferably between 50 and 150 mg ALA per 100 ml.

The weight ratio LA/ALA should be well balanced in order to prevent obesity, especially central obesity, while at the same time ensuring a normal growth and development. The proper ratio was found by the present inventors. The present composition comprises a weight ratio of LA/ALA between 2 and 7, more preferably between 3 and 6, even more preferably between 4 and 5.5, even more preferably between 4 and 5. The lipid component comprises less than 15 wt. % LA based on total fatty acids and a LA/ALA ratio of 2 to 7.

MCFA & LC-PUFA

Also n-3 LC PUFA was found to reduce both obesity and central obesity later-in-life and MCFA were found to reduce only general obesity later-in-life only. This finding further enables the development of an optimal composition, which preferably comprises MCFA, but not in excessive amounts, i.e. between 3 and 50 wt. % based on total weight of fatty acids and/or LC-PUFA including n-6 LC PUFA but with a low n-6 LC-PUFA/n-3 LC-PUFA ratio. Medium chain fatty acids (MCFA) are fatty acids and/or acyl chains with a chain length of 6, 8 or 10 carbon atoms. The present inventors also found that MCFA contribute to a reduced fat mass later in life. LA is an essential fatty acid, meaning that it cannot be synthesized within the body. As the present composition comprises a relatively low LA content, it is important that the LA included in the present composition is not converted to energy (by fat oxidation) and therefore not available for anabolic purposes. To reduce the oxidation of LA in the present low LA composition MCFA can suitably be added. MCFA are easily mobilized in the bloodstream to provide energy, rather than being stored as fat and thereby reduce LA oxidation. Therefore, the present composition preferably comprises at least 3 wt. % MCFA based on total fatty acids, more preferably at least 10 wt. %, even more preferably 15 wt. %.

The present inventors found that MCFA reduces body fat deposition with no preference for central fat mass. Therefore, the present low LA and low LA/ALA composition advantageously comprises less than 50 wt. % MCFA based on total fatty acids, more preferably less than 40 wt. %, even more preferably less than 25 wt. %.

Preferably the present composition comprises LC-PUFA. The present inventors found that LC-PUFA reduce obesity later in life, more preferably central obesity. More preferably, the present composition comprises n-3 LC-PUFA, even more preferably EPA, DPA and/or DHA, even more preferably DHA. It was found that these n-3 LC-PUFA decrease obesity.

Since a low concentration of DHA, DPA and/or EPA is already effective and normal growth and development are important, the content of n-3 LC-PUFA in the present composition, preferably does not exceed 15 wt. % of the total fatty acid content, preferably does not exceed 10 wt. %, even more preferably does not exceed 5 wt. %. Preferably the present composition comprises at least 0.2 wt. %, preferably at least 0.5 wt. %, more preferably at least 0.75 wt. % n-3 LC-PUFA of the total fatty acid content. For the same reason, the EPA content preferably does not exceed 5 wt. % of the total fatty acid, more preferably does not exceed 1 wt. %, but is preferably at least 0.025 wt. %, more preferably at least 0.05 wt. % of the total fatty acid. The DHA content preferably does not exceed 5 wt. %, more preferably does not exceed 1 wt. %, but is preferably at least 0.1 wt. % of the total fatty acid. The DPA content preferably does not exceed 1 wt. %, more preferably does not exceed 0.5 wt. % of the total fatty acid content, but is preferably at least 0.01 wt. % of the total fatty acid. Preferably as a source of n-3 LC-PUFA single cell oil, preferably algal oil, fungal oil and/or microbial oil is used, since these oil sources have a low EPA/DHA ratio, which results in an increased anti-obesity effect. More preferably the present composition comprises fish oil (more preferably tuna oil). Fish oil has a higher EPA concentration which is advantageous since EPA is precursor of eicosanoids which have an additional anti-obesity effect.

As the group of n-6 fatty acids, especially arachidonic acid (AA) and LA as its precursor, counteracts the group of n-3 fatty acids, especially DHA and EPA and ALA as their precursor, the present composition comprises relatively low amounts of AA. The n-6 LC-PUFA content preferably does not exceed 5 wt. %, more preferably does not exceed 0.8 wt. %, more preferably does not exceed 0.75 wt. %, even more preferably does not exceed 0.5 wt. % based on total fatty acids. Since AA is important in infants for optimal functional membranes, especially membranes of neurological tissues, the amount of n-6 LC-PUFA is preferably at least 0.02 wt. %, more preferably at least 0.05 wt. %, even more preferably at least 0.1 wt. % based on total fatty acids, more preferably at least 0.25 wt. %. The present composition preferably contains less than 1 wt. % AA based on total fatty acids. The presence of AA is advantageous in a composition low in LA since it remedies LA deficiency. The presence of, preferably low amounts, of AA is beneficial in nutrition to be administered to infants below the age of 6 months, since for these infants the infant formulae is generally the only source of nutrition.

The weight ratio n-6 LC-PUFA/n-3 LC-PUFA in the present infant nutrition is preferably low in order to prevent obesity later in life. Preferably the composition comprises a weight ratio of n-6 LC-PUFA/n-3 LC-PUFA below 1.5, more preferably below 1.0, even more preferably below 0.6.

LA, ALA, MCFA and/or LC-PUFA are preferably provided as free fatty acids, in triglyceride form, in diglyceride form, in monoglyceride form, in phospholipid form, or as a mixture of one of more of the above. Preferably the present composition contains LC-PUFA in triglyceride and/or phospholipid form, even more preferably phospholipid form since LC-PUFA in phospholipid form are better incorporated into membranes. Preferably, the present composition contain MCFA in triglyceride form Preferably the present composition comprises at least one, preferably at least two lipid sources selected from the group consisting of linseed oil (flaxseed oil), rape seed oil (including colza oil, low erucic acid rape seed oil and canola oil), salvia oil, perilla oil, purslane oil, lingonberry oil, sea buckthorn oil, hemp oil, high oleic sunflower oil, high oleic safflower oil, olive oil, marine oils, microbial oils, black currant seed oil, echium oil, butter fat, coconut oil and palm kernel oil. Preferably the present composition comprises at least one, preferably at least two lipid sources selected from the group consisting of linseed oil, rapeseed oil, coconut oil, high oleic sunflower oil, butter oil and marine oil.

Table 1 gives preferred characteristics of the lipid component of the present composition

TABLE 1

|  | preferred | more preferred | most preferred |
| --- | --- | --- | --- |
| LA (wt. % based on total fatty acids) | <15 | 5-14.5 | 6-12 |
| ALA (wt. % based on total fatty acids) | >1 | 1.6-10 | 2.0-5.0 |
| Weight ratio LA/ALA | 2-7 | 3-6 | 4-5.5 |
| MCFA (wt. % based on total fatty acids) | 3-50 | 10-40 | 15-25 |
| N-6 LC-PUFA (wt. % based on total fatty acids, sum of AA + DHGLA) | 0.02-0.8 | 0.05-0.75 | 0.25-0.5 |
| n-3 LC-PUFA (wt. % based on total fatty acids, sum of EPA, DPA and DHA) | >0.2 | 0.25-15 | 0.75-5 |
| Ratio n-6 LC-PUFA/n-3 LC-PUFA | <1.5 | <1.0 | <0.6 |

Phospholipids, Cholesterol and Sphingolipids

Since LA is an essential fatty acid and n-6 LC-PUFA are important membrane components (including in neurological tissue membranes), the small amount of LA and optionally n-6 LC-PUFA present in the composition of the invention are preferably incorporated into neurological cell membranes as efficiently as possible. This can be achieved by providing lipidic membrane components, including cholesterol, phospholipids and/or sphingolipids in the present low LA composition. The presence of these components increases the incorporation of PUFA, including LA and n-6 LC-PUFA in membranes, thereby preventing oxidation.

The term phospholipids as used in the present invention particularly refers to glycerophospholipids. Glycerophospholipids are a class of lipids formed from fatty acids esterified to the hydroxyl groups on carbon-1 and carbon-2 of the backbone glycerol moiety and a negatively-charged phosphate group attached to carbon-3 of the glycerol via an ester bond, and optionally a choline group (in case of phosphatidylcholine), a serine group (in case of phosphatidylserine), an ethanolamine group (in case of phosphatidylethanolamine), an inositol group (in case of phosphatidylinositol) or a glycerol group (in case of phosphatidylglycerol) attached to the phosphate group. Preferably the present composition contains phosphatidylcholine (PC), phosphatidylserine, phosphatidylinositol and/or phosphatidylethanolamine, more preferably at least phosphatidylcholine.

A preferred source for phospholipids, particularly PC, is soy lecithin, egg lipid, and/or buttermilk fat. Hence the present composition preferably comprises soy lecithin, egg lipid and/or buttermilk fat, more preferably soy lecithin and/or buttermilk fat.

Preferably the present composition comprises 0.5 to 20 wt. % phospholipids based on total lipid, more preferably 1 to 10 wt. %, even more preferably 4 to 8 wt %. As also found by the inventors, oral administration of a composition comprising phospholipids and/or sphingolipids and/or cholesterol has the further advantage that it decreases the post-prandial insulin response (see example 2). High insulin levels stimulate glucose uptake in adipose tissue, resulting in an increased adipose tissue mass. In infants high insulin levels also contribute to increased visceral adipocyte proliferation, at least partly due to the increased glucose uptake. Therefore the present composition for infants aimed to decrease obesity later in life preferably comprises phospholipids, sphingolipids and/or cholesterol, more preferably phospholipids.

Preferably the present composition comprises 0.5 to 20 wt. % sphingolipids based on total lipid, more preferably 1 to 10 wt. %, even more preferably 4 to 8 wt. %. The term sphingolipids as in the present invention refers to glycolipids with an amino alcohol sphingosine. The sphingosine backbone is O-linked to a (usually) charged head group such as ethanolamine, serine or choline backbone. The backbone is also amide linked to a fatty acyl group. Sphingolipids include sphingomyelin, ceramides, and glycosphingolipids. Preferably the present composition contains sphingomyelin and/or glycosphingolipids. Glycosphingolipids are ceramides with one or more sugar residues joined in a β-glycosidic linkage at the 1-hydroxyl position. Glycosphingolipids may be further subdivided into cerebrosides, globosides and gangliosides. Cerebrosides have a single glucose or galactose at the 1-hydroxy position, while gangliosides have at least three sugars, one of which must be sialic acid. Sphingomyelins have a phosphorylcholine or phosphoroethanolamine molecule esterified to the 1-hydroxy group of a ceramide. Preferably the present composition contains gangliosides.

Preferably the composition comprises sphingolipids, more preferably sphingomyelin and/or gangliosides. Preferably the present composition comprises at least one ganglioside selected from the group consisting of GM3 and GD3.

Preferably the present composition comprises 0.5 to 20 wt. % (sphingolipids plus phospholipids) based on total lipid, more preferably 1 to 10 wt. %, even more preferably 4 to 8 wt. %.

Dietary cholesterol modulates lipid metabolism by the stimulation of chain elongation of the fatty acyl chains (phospholipids, free fatty acids; diglycerides and triglycerides). By affecting the conversion of essential fatty acids to their LC-PUFA successors, the production of essential membrane building block is increased and thus the synthesis and function of neuronal membranes in the brain. Consequently, the use of essential lipids for energy metabolism is reduced. Furthermore, cholesterol is an essential building block of membranes, and is necessary to increase membrane synthesis. Cholesterol is therefore advantageously included in the present low LA composition to prevent side effects of the low LA in the present formula.

Moreover, dietary cholesterol during infancy inhibits the endogenous cholesterol synthesis and programs the endogenous cholesterol synthesis to lower levels. Consequently, reduced blood cholesterol levels later in life will be achieved. This results in a drop of LDL-cholesterol value in blood and a raise of HDL cholesterol value in blood during adolescent and adulthood. Hence the present invention also provides the use of a composition comprising a lipid, protein, digestible carbohydrate and cholesterol for the manufacture of a nutritional composition to be administered to an infant with the age below 36 months for the prevention of cardiovascular disease, atherosclerosis and/or high blood cholesterol levels later in life. This nutritional composition preferably has at least part of the nutrient requirement described in the present application, e.g. advantageously includes the non-digestible oligosaccharide, lactose and/or lipid component as described herein.

Preferred sources of cholesterol are milk fat, buttermilk fat, butterserum fat and egg lipids. Hence the present composition preferably comprises buttermilk fat, butterserum fat and/or egg lipids. The present composition preferably comprises at least 0.005 wt. % cholesterol based on total fat, more preferably at least 0.01 wt. %, more preferably at least 0.05 wt. %., even more preferably at least 0.1 wt. %. Preferably the amount of cholesterol does not exceed 10 wt. % based on total lipid, more preferably does not exceed 5 wt. %, even more preferably does not exceed 1 wt. % of total lipid. Most preferably the amount of cholesterol is 0.5 to 0.7 wt. % based on total lipid.

Preferably the amount of cholesterol does not exceed 1 wt. % based on total fat, more preferably does not exceed 0.5 wt. %.

Uridine and Choline

Alternatively, the present low LA composition comprises a source of uridine and choline. In humans receiving the present low LA composition, enhanced membrane synthesis is preferably achieved by providing the two main precursors for phosphatidyl choline or other major membrane phospholipids in brain, namely a source of uridine and choline. Uridine is metabolized to cytidine and subsequently phosphorylated to CTP; choline is metabolized to phosphocholine. Subsequently, CTP and phosphocholine result in CDP-choline formation, a key step in phospholipid biosynthesis pathway. Thus, the combination of a source of uridine and choline stimulate phospholipid biosynthesis. The increase of phospholipid synthesis caused by uridine and choline supplementation also enhances the incorporation of arachidonic acids and other LC-PUFA into the mayor phospholipids in the brain, which makes it particularly suitable for counteracting side effects of the present low LA composition.

Preferably the composition comprises a source of uridine and choline. Choline is preferably added as choline chloride. The present composition preferably comprises choline chloride. The present composition preferably comprises at least 0.035 wt. % choline based on dry weight of the composition, more preferably at least 0.045 wt. %. Preferably the present composition comprises no more than 1 wt. % choline based on total dry weight or the present composition, more preferably below 0.5 wt. %, even more preferably below 0.1 wt. %.

The presence of choline has the further advantage that it oxidizes fat, results in an increase of lean body mass and enhances the fat clearance of blood into cells. Choline has the further advantage that it is an excellent methyl donor. In stages of quick growth such as in infancy, a sufficient amount of methyl donor is important to sustain differentiation and regulation and thereby result in a proper metabolic imprinting via DNA methylation. A proper metabolic imprinting is important for preventing obesity later in life. Therefore the composition of the present invention preferably comprises choline.

In a preferred embodiment the present composition comprises uridine in the form of a nucleotide, nucleoside and/or base. Preferably the composition comprises 0.001 to 0.1 wt. % uridine based on dry weight of the present composition, more preferably 0.002 to 0.05 wt. %, most preferably 0.002 to 0.025 wt. %. More preferably the composition comprises uridine in nucleotide form. The uridine is preferably in the nucleotide monophosphate, diphosphate or triphosphate form, more preferably in nucleotide monophosphate form. The uridine nucleotides can be monomeric, dimeric or polymeric (including RNA). The nucleotides preferably are present as a free acid or in the form of a salt, more preferably monosodium salt. Preferably, the present composition comprises uridine 5'-monophospate and/or salts thereof (collectively abbreviated to UMP), in particular monosodium salts thereof. Preferably the composition comprises 0.001 to 0.1 wt. % UMP based on dry weight of the present composition, more preferably 0.002 to 0.05 wt. %, most preferably 0.002 to 0.025 wt. %. UMP is preferably be added to the composition in a mixture of nucleotides.

Preferably the present composition contains yeast RNA as a source of UMP. Preferably the composition comprises UMP and choline. Preferably the composition comprises a source of uridine, choline and phospholipids. Preferably the composition comprises UMP, choline and phospholipids. This combination even further stimulates membrane formation and is therefore particularly suitable for inclusion in the present low LA composition.

Non-Digestible Oligosaccharides

As already described above high blood insulin levels stimulate glucose uptake in adipose tissue, resulting in an increased adipose tissue mass. In infants the high insulin levels contribute to increased proliferation of adipocytes, at least partly due to the increased glucose uptake, and thereby in an increased chance of obesity later in life.

The present composition therefore preferably maintains low insulin levels. It was found that non-digestible oligosaccharides (NDO) that can be fermented (particularly galacto-oligosaccharides) have a blood insulin tempering effect, and consequently contribute to a reduced change on obesity later-in-life. Additionally it was also recognized that infants ingest more calories when bottle fed compared to a situation where breast feeding occurs. In addition to the compositional features of the lipid component as suggested in the present invention, the effectiveness can further be improved by reducing caloric intake. Limiting dosage of the nutritional composition is however not a feasible option for infants. The present inventors have found that for this purpose advantageously the present composition comprises non-digestible oligosaccharides. Fermentation of these non-digestible oligosaccharides, preferably galacto-oligosaccharides, further results in the formation of intestinal acetate which is taken up and will enter the circulation and the liver, thereby serving advantageously as a lipid elongation precursor and/or advantageously stimulating the conversion of LA to AA.

Therefore, the present composition preferably comprises the present lipid component and a non-digestible oligosaccharide which can be fermented. The combination of the present lipid component and the non-digestible oligosaccharides synergistically reduces the obesity later in life. Preferably the present composition comprises non-digestible oligosaccharides that have a DP between 2 and 60. The composition preferably prevents the onset of insulin resistance. The non-digestible oligosaccharide is preferably selected from the group consisting of fructo-oligosaccharides (including inulin), galacto-oligosaccharides (including transgalacto-oligosaccharides), gluco-oligosaccharides (including gentio-, nigero- and cyclodextrin-oligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides. Preferably the present composition comprises fructo-oligosaccharides, galacto-oligosaccharides and/or galacturonic acid oligosaccharides, more preferably galacto-oligosaccharides, most preferably transgalacto-oligosaccharides. In a preferred embodiment the composition comprises a mixture of trans-galacto-oligosaccharides and fructo-oligosaccharides. Preferably the present composition comprises galacto-oligosaccharides with a DP of 2-10 and/or fructo-oligosaccharides with a DP of 2-60. The galacto-oligosaccharide is preferably selected from the group consisting of transgalacto-oligosaccharides, lacto-N-tetraose (LNT), lacto-N-neotetraose (neo-LNT), fucosyl-lactose, fucosylated LNT and fucosylated neo-LNT. In a particularly preferred embodiment the present method comprises the administration of transgalacto-oligosaccharides ([galactose]$_n$-glucose; wherein n is an integer between 1 and 60, i.e., 2, 3, 4, 5, 6, . . . , 59 ,60; preferably, n is 2, 3, 4, 5, 6, 7, 8, 9, or 10). Transgalacto-oligosaccharides (TOS) are for example sold under the trademark Vivinal™ (Borculo Domo Ingredients, Netherlands). Preferably the saccharides of the transgalacto-oligosaccharides are β-linked. Fructo-oligosaccharide is a NDO comprising a chain of β linked fructose units with a DP or average DP of 2 to 250, more preferably 10 to 100. Fructo-oligosaccharide includes inulin, levan and/or a mixed type of polyfructan. An especially preferred fructo-oligosaccharide is inulin. Fructo-oligosaccharide suitable for use in the compositions is also already commercially available, e.g. Raftiline®HP (Orafti). Uronic acid oligosaccharides are preferably obtained from pectin degradation. Hence the present composition preferably comprises a pectin degradation product with a DP between 2 and 100. Preferably the pectin degradation product is prepared from apple pectin, beet pectin and/or citrus pectin. Preferably the composition comprises transgalacto-oligosaccharide, fructo-oligosaccharide and a pectin degradation product. The weight ratio transgalacto-oligosaccharide : fructo-oligosaccharide : pectin degradation product is preferably 20 to 2:1:1 to 3, more preferably 12 to 7:1:1 to 2.

Lactose

The maintenance of insulin sensitivity can be further improved by inclusion of a low glycemic carbohydrate in the present composition, preferably lactose. Hence, the present composition preferably comprises in addition to the present lipid component, non-digestible oligosaccharides and/or lactose. The present composition preferably comprises a digestible carbohydrate component, wherein at least 35 wt. %, more preferably at least 50 wt. %, more preferably at least 75 wt. %, even more preferably at least 90 wt. %, most preferably at least 95 wt. % is lactose. The present composition preferably comprises at least 25 grams lactose per 100 gram dry weight of the present composition, preferably at least 40 grams lactose/100 gram.

Hydrolyzed Protein

Preferably the composition comprises hydrolyzed casein and/or hydrolyzed whey protein. It was found that administration of a composition wherein the protein comprises hydrolyzed casein and hydrolyzed whey results in reduced post-prandial levels of both insulin and glucose compared to the administration of a composition comprising intact casein and intact whey protein. Increased levels of both insulin and glucose indicate a form of insulin resistance in formula fed infants, which is believed contribute to the development of obesity later-in-life. The present composition preferably comprises at least 25 wt. % peptides with a chain length of 2 to 30 amino acids based on dry weight of protein. The amount of peptides with a chain length between 2 and 30 amino acids can for example be determined as described by de Freitas et al., 1993, J. Agric. Food Chem. 41:1432-1438. The present composition preferably comprises casein hydrolysate and/or whey protein hydrolysate, more preferably casein hydrolysate and whey protein hydrolysate because the amino acid composition of bovine casein is more similar to the amino acid composition found in human milk protein and whey protein is easier to digest and found in greater ratios in human milk. The composition preferably comprises at least 50 wt. %, preferably at least 80 wt. %, most preferably about 100 wt. % of a protein hydrolysate, based on total weight of the protein. The present composition preferably comprises a protein with a degree of hydrolysis of the protein between 5 and 25%, more preferably between 7.5 and 21%, most preferably between 10 and 20%. The degree of hydrolysis is defined as the percentage of peptide bonds which have been broken down by enzymatic hydrolysis, with 100% being the total potential peptide bonds present.

Casein

Casein is advantageously present since it increases the gastric emptying times by forming a curd in the stomach, thereby increasing satiety. As satiety induction is highly desirable, see above, the present composition preferably comprises casein. When the composition is in liquid form, e.g., as a ready-to-drink liquid, the composition preferably comprises at least 0.5 g casein per 100 ml, preferably between 0.5 and 5 gram casein per 100 ml. Preferably the composition comprises at least 4 wt. % casein based on dry weight. Preferably the casein is intact and/or non-hydrolyzed.

Calcium

Preferably the composition comprises calcium. Increased dietary calcium decreases the intracellular calcium concentration in adipocytes and this may in decrease adipocytes late stage differentiation and lipid filling. Preferably the calcium is added with as counter anion carbonate, hydroxide, chloride, phosphate, lactate, gluconate, and/or citrate. Preferably the composition comprises at least 0.1 wt. % calcium based on dry weight of the composition, preferably at least 0.25 wt. % most preferably at least 0.4 wt. %. Preferably the composition comprises less than 5 wt. % calcium based on dry weight of the composition, preferably less than 2 wt. %, more preferably less than 1 wt. %.

Nutritional Composition

The present composition is particularly suitable for providing the daily nutritional requirements to an infant with the age below 36 months, particularly an infant with the age below 24 months, even more preferably an infant with the age below 18 months, most preferably below 12 months of age. Hence, the present composition comprises a lipid, protein and digestible carbohydrate component wherein the lipid component provides preferably 35 to 55% of the total calories, the protein component preferably provides 5 to 15% of the total calories and the digestible carbohydrate component preferably provides 30 to 60% of the total calories. Preferably the present composition comprises a lipid component providing 40 to 50% of the total calories, a protein component provides 6 to 12% of the total calories and a digestible carbohydrate component provides 40 to 50% of the total calories. When in liquid form, e.g. as a ready-to-feed liquid, the composition preferably comprises 2.1 to 6.5 g lipid per 100 ml, more preferably 3.0 to 4.0 g per100 ml. Based on dry weight the present composition preferably comprises 12.5 to 40 wt. % lipid, more preferably 19 to 30 wt. %.

The amount of saturated fatty acids is preferably below 58 wt. % based on total fatty acids, more preferably below 45 wt. %. The concentration of monounsaturated fatty acids preferably ranges from 17 to 60% based on weight of total fatty acids.

The present composition is not human breast milk. The present composition preferably comprises (i) vegetable lipid and/or animal (non-human) fat; and/or (ii) vegetable protein and/or animal (non-human) milk protein. Examples of animal milk protein are whey protein from cow's milk and protein from goat milk. The present composition preferably does not comprise a proteinase inhibitor, preferably not a trypsin inhibitor, chymotrypsin inhibitor or elastase inhibitor. The present composition is not human milk.

The present composition preferably comprises at least 50 wt. % protein derived from non-human milk based on total protein, more preferably at least 90 wt. %. Preferably the present composition comprises at least 50 wt. % cow's milk derived protein based on total protein, more preferably at least 90 wt. %. Preferably the present composition comprises acid whey and/or sweet whey with a reduced concentration of glycomacropeptide. Preferably the present composition comprises protein derived from β-casein and/or α-lactalbumin. The present composition preferably comprises casein and whey proteins in a weight ratio casein:whey of 10:90 to 90:10, more preferably 20:80 to 80:20. The term protein as used in the present invention refers to the sum of proteins, peptides and free amino acids. The present composition preferably contains 1.5 to 3.0 g protein/100 kcal, preferably between and 1.8 and 2.25 g/100 kcal, even more preferably between and 1.8 and 2.0 g/100 kcal.

The present composition is preferably administered in liquid form. In order to meet the caloric requirements of the infant, the composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present composition is preferably between 150 and 420 mOsmol/l, more preferably 260 to 320 mOsmol/l. The low osmolarity aims to reduce the gastrointestinal stress. Stress can induce obesity.

Preferably the composition is in a liquid form, with a viscosity below 35 cps as measured in a Brookfield viscometer at 20° C. at a shear rate of 100 s$^{-1}$. Suitably, the composition is in a powdered from, which can be reconstituted with water to form a liquid, or in a liquid concentrate form, which should be diluted with water.

When the composition is a liquid form, the preferred volume administered on a daily basis is in the range of about 80 to 2500 ml, more preferably about 450 to 1000 ml per day.

Infants

Adipocytes, including visceral adipocytes, proliferate during the first 36 months of life as well as (more limited) in puberty. The amount of adipocytes is an important determinant in the degree of obesity later-in-life. Hence the present composition is administered to the infant during the first 3 years of life. It was found that there is a predominance of proliferation of (visceral) adipocytes in the first 12 months of life (with an optimum in perinatal adipocyte proliferation). Hence, it is particularly preferred that the present composition is administered to the infant in this period of life. The present composition is therefore advantageously administered to a human of 0-24 months, more preferably to a human of 0-18 months, most preferably to a human of 0-12 months. The present invention particularly aims to prevent obesity later-in-life and is preferably not an obesity treatment. Hence, the present composition is preferably administered to an infant not suffering from obesity or childhood obesity, particularly a non-obese infant more preferably an infant that does not suffer from overweight. The present composition is preferably administered orally to the infant.

Applications

The composition of the present invention relates to a method for preventing obesity in a human with the age below 36 months. The present invention also aims to prevent the occurrence of obesity at the age above 36 months, particularly to prevent obesity at the age above 8 years, particularly above 15 years, more particularly above 18 years.

Preferably the composition is used to prevent obesity, more preferably central obesity (i.e. obesity), since especially central obesity is related to health disorders such as cardiovascular diseases, hypertension and diabetes.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Example 1

Programming Effect of Dietary Lipid on Adult Fat Tissue

Offspring of C57/BL6 dams was standardized on postnatal day 2 to nests of 6 pups (4M and 2F) per dam. Dams were fed the experimental diet from day 2 onward until weaning. The lipid composition of the mouse milk reflects the fat composition of the diet. After weaning the male mice were housed in pairs and the experimental diet was continued until day 42 when all pups were fed the same diet containing lard and extra cholesterol (1%).

The experimental diets that were used were: 1) LC-PUFA diet (tuna fish oil); 2) Low LA, low LA/ALA diet (butter oil; low in canola oil, high in Trisun 80, no palm oil); 3) MCFA diet; 4) control diet (similar amounts of canola oil, coconut oil and palm oil). The fatty acid composition of the diets is presented in Table 2. At day 42, all mice switched to a "cafeteria diet" comprising 10 wt. % lipid (3 wt. % lard fat and 1wt. % cholesterol) until day 98. The mice were weighed twice a week. The food intake was determined once a week during the entire experiment. To determine body composition (i.e., fat mass (FM) and fat-free mass (FFM)) DEXA scans (Dual Energy X-ray Absorbometry) were performed under general anesthesia at 6, 10 and 14 weeks of age, 42, 70 and 98 days after birth respectively, by densitometry using a PIXImus imager (GE Lunar, Madison, Wis., USA). At the age of 14 weeks the male mice were sacrificed and plasma, epididymal fat, renal fat, pancreas, liver and kidneys were dissected and weighed.

Results: No effect on growth and food intake was observed during the experimental period between the groups (data not shown). Moreover, the development of fat mass (determined with DEXA) was not different at day 42 (end of the diet intervention period). However, a subsequent treatment with a cafeteria diet (high in saturated fatty acids) between day 42 and day 98 of all groups resulted in clear differences in body composition at the end of the experiment (day 98), see Table 3. The fat mass was reduced when the pups received a LC-PUFA, MCFA or low LA, low LA/ALA diet in their early life, compared to the control diet. Moreover, the diets in early life had markedly effect on the body fat distribution. It was shown that the ratio of the subcutaneous:visceral fat (measured by epididymal and renal fat, respectively) in adult mice at day 98 was increased by 14% in the LC-PUFA group and 32% in the low LA group, but was not increased in the MCFA group compared to the control group, see Table 3. This demonstrated

TABLE 2

Fatty Acid Composition of the Diets

|  |  | control g/100 g fat | MCFA g/100 g fat | LC-PUFA g/100 g fat | Low LA g/100 g fat | Cafeteria g/100 g fat |
|---|---|---|---|---|---|---|
| C-4:0 |  | 0.00 | 0.00 | 0.00 | 1.05 | 0.00 |
| C-6:0 |  | 0.11 | 0.15 | 0.07 | 0.81 | 0.06 |
| C-8:0 |  | 1.70 | 11.42 | 1.07 | 2.09 | 0.85 |
| C-10:0 |  | 1.36 | 8.77 | 0.86 | 2.17 | 0.68 |
| C-12:0 |  | 10.53 | 1.34 | 6.69 | 11.42 | 5.27 |
| C-14:0 |  | 4.38 | 0.75 | 3.62 | 7.24 | 2.69 |
| C-14:1w5 |  | 0.00 | 0.00 | 0.00 | 0.00 | 0.00 |
| C-15:0 |  | 0.00 | 0.00 | 0.00 | 0.00 | 0.00 |
| C-16:0 |  | 17.14 | 13.35 | 19.38 | 12.40 | 23.07 |
| C-16:1w7 |  | 0.13 | 0.12 | 1.20 | 0.78 | 1.56 |
| C-17:0 |  | 0.00 | 0.00 | 0.37 | 0.00 | 0.00 |
| C-18:0 |  | 3.07 | 2.39 | 3.70 | 5.12 | 9.03 |
| C-18:1w9 |  | 37.94 | 38.52 | 35.27 | 40.79 | 40.47 |
| C-18:2w6 | LA | 14.80 | 14.31 | 11.89 | 6.38 | 11.90 |
| C-18:3w3 | ALA | 2.61 | 2.61 | 1.07 | 1.57 | 1.30 |
| C-18:3w6 |  | 0.00 | 0.00 | 0.00 | 0.00 | 0.00 |
| C-18:4w3 |  | 0.00 | 0.00 | 0.19 | 0.00 | 0.00 |
| C-20:0 |  | 0.34 | 0.34 | 0.26 | 0.20 | 0.17 |
| C-20:1w9 |  | 0.41 | 0.41 | 0.15 | 0.22 | 0.21 |
| C-20:2w6 |  | 0.00 | 0.00 | 0.00 | 0.00 | 0.00 |
| C-20:3w6 |  | 0.00 | 0.00 | 0.00 | 0.00 | 0.00 |
| C-20:4w3 |  | 0.00 | 0.00 | 0.07 | 0.00 | 0.00 |
| C-20:4w6 | AA | 0.00 | 0.00 | 0.28 | 0.00 | 0.00 |
| C-20:5w3 | EPA | 0.00 | 0.00 | 1.20 | 0.00 | 0.00 |
| C-22:0 |  | 0.23 | 0.28 | 0.24 | 0.33 | 0.11 |
| C-22:1w9 |  | 0.14 | 0.14 | 0.05 | 0.08 | 0.07 |
| C-22:4w6 |  | 0.00 | 0.00 | 0.00 | 0.00 | 0.00 |
| C-22:5w3 | DPA | 0.00 | 0.00 | 0.37 | 0.00 | 0.00 |
| C-22:6w3 | DHA | 0.00 | 0.00 | 5.00 | 0.00 | 0.00 |
| C-24:0 |  | 0.02 | 0.02 | 0.02 | 0.00 | 0.01 |
| C-24:1w9 |  | 0.00 | 0.00 | 0.00 | 0.00 | 0.00 |
| cholesterol |  |  |  |  |  | 1.00 |
| Total |  | 94.91 | 94.92 | 93.02 | 92.66 | 98.46 | that the visceral fat mass in later life clearly is decreased by an early in life diet high in LC-PUFA and/or low in LA and/or low LA/ALA. So, it is concluded that these fat compositions program and/or imprint the body to get a healthier body fat composition later-in-life. So, it is concluded that these fat compositions program and/or imprint the body to prevent obesity later-in-life.

TABLE 3

Fat % development of total body mass in time and ratio's of subcutaneous (epididymal) and central (renal) fat.

| | Day | Control diet | MCFA diet | LC-PUFA diet | Low LA diet |
|---|---|---|---|---|---|
| Fat mass (%) | 42 | 19.6 | 17.1 | 16.6 | 17.1 |
| Fat mass (%) | 70 | 22.1 | 22.8 | 21.5 | 24.2 |
| Fat mass (%) | 98 | 26.9 | 22.8 | 20.9 | 24.2 |
| Ratio subcutaneous/visceral fat | 98 | 7.54 | 7.2 | 8.59 | 9.92 |
| Ratio increase (%) | | | −4% | +14% | +32% |

Example 2

Phospholipids Beneficially Affect Insulin Sensitivity

Nutritional compositions: A complete infant formula with extra added phospholipids (0.2 g/100 ml) was manufactured using a commercially available buttermilk/butterserum concentrate of Lactalis as source. An infant formula with a comparable composition, but without added phospholipids was used as control. The concentration of phospholipids was about 6.3 wt. % based on total lipid in the experimental formula and about 0.75 wt. % based on total lipid in the control formula. The experimental composition comprised about 1.4 wt. % sphingomyelin based on total lipid and about 4 wt. % cholesterol based on total lipid. The amount of sphingomyelin and cholesterol was negligible in the control formula.

Methods: 20 adult male Wistar rats (aged 10 weeks at the start of the experiment) were housed individually. After a 4 h fasting period, 10 animals were fed 2 ml of a composition. Three different compositions were tested in a cross-over design (experiments separated by one week) i) Standard infant formula, ii) Phospholipid comprising formula. Subsequently, blood samples (200 µl) were collected in heparinized chilled tubes at t=0, 5, 10, 15, 30, 60 after feeding. Subsequently, plasma was separated after centrifugation (10 min, 5000 rpm) and stored at −20° C. until analysis. Plasma insulin was measured by radioimmunoassay (RIA, of Linco Research) according to the manufacturer's instructions with the following adjustment: all assay volumes were reduced four times.

Results: The area under the curve (AUC) of insulin was lower in rats fed phospholipid containing formula than in rats fed with standard formula. (Table 4). Administration of a phospholipid, sphingolipid and/or cholesterol comprising formula resulted in post-prandial insulin levels and kinetics more similar to those previously observed with human milk. Decreased levels of insulin indicate increased insulin sensitivity, which is believed contribute to the prevention of obesity, especially central obesity, later-in-life.

TABLE 4

Effects of phospholipids on post-prandial area under the curve (AUC) of insulin

| Effect | Standards | Phospholipids | Human Milk |
|---|---|---|---|
| AUC 10 (±SE) | | | |
| Insulin (pM * 10 min) | 9.8 ± 1.4 | 9.5 ± 1.0 | |
| AUC 15 (±SE) | | | |
| Insulin (pM * 15 min) | 14.8 ± 2.1 | 13.8 ± 1.6 | |
| AUC 30 (±SE) | | | |
| Insulin (pM * 30 min) | 21.4 ± 2.9 | 18.7 ± 2.0 | 1.7 ± 4.7 |
| AUC 60 (±SE) | | | |
| Insulin (pM * 60 min) | 25.8 ± 3.3 | 23.6 ± 2.2 | |

Example 3

Blood Glucose/Insulin and Non-Digestible Oligosaccharides

Animals and treatment: Adult male Wistar rats (n=7) were given a GOS fiber load, cellulose load or water via a gastric cannula on day 1. A 6 ml bolus load was administered equal to 50% of their daily fiber intake; GOS fiber used was trans-galacto-oligosaccharides obtained from Elix'or (Borculo Domo). Fiber was dissolved in water. About 24 h later (on day 2) an oral glucose tolerance test was carried out and the postprandial glucose and insulin course was monitored for 120 min upon the intragastric injection of a carbohydrate load (2 g/kg body weight). To this end blood samples were drawn repeatedly via a jugular vein cannula. Intragastric injection of water or a cellulose solution in water on day 1 served as control. As the GOS fiber preparation consisted of 50% of digestible carbohydrates (mainly lactose), the two control injections were co-administered with carbohydrates to correct for this.

Results: pre-treatment with GOS fibers clearly decreased the amount of insulin secreted, resulting in significant ($p<0.05$) lower incremental AUC values. Blood glucose levels were not affected significantly. Pre-treatment with cellulose or water did not modulate the insulin secretion, see Table 5.

TABLE 5

Insulin and glucose Levels in Rats

| Pre-treatment with: | AUC insulin (pM * 30 min) | AUC glucose (mM * 30 min) |
|---|---|---|
| Water | 41 ± 7 | 69 ± 10 |
| Cellulose | 46 ± 8 | 75 ± 9 |
| GOS | 22 ± 4 | 74 ± 15 |

Example 4

Infant Nutrition

Infant nutrition comprising a lipid component providing 48% of the total calories, a protein component providing 8% of the total calories and a digestible carbohydrate component providing 44% of the total calories; (i) the lipid component comprising based on total fatty acids: 14 wt. % LA; 2.6 wt. % ALA, 3.7 wt. % MCFA; 0.2 wt. % DHA, 0.05 wt. % EPA; 0.02 wt. % DPA, 0.35 wt. % AA, 0.03 wt. % DHGLA. Based on total fat the composition comprises about 0.75 wt. % soy phospholipids and >0.005 wt. % cholesterol. (ii) the carbohydrate component comprising 50.9 gram lactose/100 gram powder; 5.22 g galacto-oligosaccharides with DP 2-6 and 0.58 g fructo-oligosaccharides with DP 7-60; (ii) the protein component comprising cow milk protein, including casein. Furthermore the composition comprises 73 mg choline and 5.6 mg UMP per 100 g dry weight. The composition comprises 364 mg calcium per 100 g dry weight. The composition comprises vitamins and minerals according to EU guidelines. The label of the package of this infant nutrition indicates that the nutrition prevents the development of obesity.

We claim:

1. A method to reduce the risk of developing cardiovascular disease, atherosclerosis, and/or high blood cholesterol levels in a non-obese human infant, comprising feeding a human infant younger than 36 months of age with a composition comprising a lipid, a protein, and a digestible carbohydrate, wherein the lipid component comprises:
   (i) linoleic acid (LA) and α-linolenic acid (ALA) in a weight ratio of LA to ALA of between 2 and 7;
   (ii) less than 15 weight (wt.) % LA based on weight of total fatty acids in the composition; and
   (iii) at least 1 wt. % ALA based on weight of total fatty acids in the composition,
   (iv) 0.005 to 10 wt. % cholesterol based on weight of total lipid in the composition, which composition further comprises:
   (a) 0.5 to 20 wt. % phospholipids based on weight of total lipid in the composition; and/or
   (b) 0.5 to 20 wt. % sphingolipids based on weight of total lipid in the composition, and wherein the digestible carbohydrate comprises at least 35 wt. % lactose.

2. The method according to claim 1, wherein the composition comprises less than 10 wt. % ALA, based on weight of total fatty acids in the composition.

3. The method according to claim 1, wherein the composition comprises between 5 wt. % and 15 wt. % LA based on total fatty acids in the composition.

4. The method according to claim 1, wherein the composition comprises at least 0.01 wt. % cholesterol and no more than 10 wt. % cholesterol based on total lipid in the composition.

5. The method according to claim 1, wherein the composition comprises at least 3wt. % medium chain fatty acids (MCFA) based on total fatty acids in the composition.

6. The method according to claim 1, wherein the composition comprises between 0.2 wt. % and 15 wt. % n-3 long chain polyunsaturated fatty acids (LC-PUFA) based on total fatty acids in the composition.

7. The method according to claim 1, wherein the composition comprises between 0.02 wt. % and 5 wt. % n-6 LC-PUFA based on total fatty acids in the composition.

8. The method according to claim 1, wherein
   (a) the lipid provides 35 % to 55 % of the total calories of the composition,
   (b) the protein provides 5 % to 15 % of the total calories of the composition; and
   (c) the digestible carbohydrate provides 30 % to 60 % of the total calories of the composition.

9. The method according to claim 1, wherein the composition provides 60 -90 kcal/100 ml.

10. The method according to claim 1, wherein the feeding is of an infant with an age below 12 months.

11. The method according to claim 1, wherein the composition further comprises at least 0.5 wt. % of at least one soluble, non-digestible oligosaccharide based on dry weight of the composition.

12. The method according to claim 11, wherein the soluble, non-digestible oligosaccharide is selected from the group consisting of a fructo-oligosaccharide, a galacto-oligosaccharide, a gluco-oligosaccharide, an arabino-oligosaccharide, a mannan-oligosaccharide, a xylo-oligosaccharide, a fuco-oligosaccharide, an arabinogalacto-oligosaccharide, a glucomanno-oligosaccharide, a galactomanno-oligosaccharide, sialic acid comprising an oligosaccharide and a uronic acid oligosaccharide.

13. The method according to claim 12, wherein the soluble, non-digestible oligosaccharide is a galacto-oligosaccharide.

14. The method according to claim 12, wherein the soluble, nondigestible oligosaccharide is a fructo-oligosaccharide.

15. The method according to claim 12, wherein the soluble, non-digestible oligosaccharide is a galacto-oligosaccharides and a fructo-oligosaccharide.

16. The method of claim 1, wherein the composition further comprises:
   (v) 0.035 to 1 wt. % choline based on dry weight of the composition; and
   (vi) 0.001 to 0.1 wt. % uridine based on dry weight of the composition.

17. The method of claim 16 wherein the uridine is in the form of uridine monophosphate.

18. The method of claim 1 wherein the feeding of said infant reduces the risk of development of cardiovascular disease, atherosclerosis, and/or high blood cholesterol levels at an age above 36 months.

* * * * *